United States Patent [19]

Smolanoff

[11] 4,455,308

[45] * Jun. 19, 1984

[54] ARTHROPOD REPELLENTS

[75] Inventor: Joel R. Smolanoff, Chalfont, Pa.

[73] Assignee: Rohm and Haas Company, Philadelphia, Pa.

[*] Notice: The portion of the term of this patent subsequent to Jun. 21, 2000 has been disclaimed.

[21] Appl. No.: 426,522

[22] Filed: Sep. 29, 1982

Related U.S. Application Data

[62] Division of Ser. No. 56,179, Jul. 10, 1979, Pat. No. 4,389,401.

[51] Int. Cl.³ .................. A01N 47/28; A01N 47/38
[52] U.S. Cl. ............................ 424/248.57; 424/322; 560/169
[58] Field of Search .................. 424/248.55, 274, 314, 424/322, 248.57; 544/67; 564/58, 57; 560/169; 548/538

[56] References Cited

U.S. PATENT DOCUMENTS 2,928,855  3/1960  Yale .................................. 260/431

OTHER PUBLICATIONS

Forman et al., J. Org. Chem., vol. 28, (1963), pp. 2653–2658.

*Primary Examiner*—Richard Raymond
*Attorney, Agent, or Firm*—Terence P. Strobaugh; William E. Lambert, III

[57] ABSTRACT

This invention relates to novel compounds of the formula

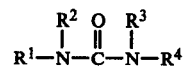

wherein $R^1$ is lower alkenyl or lower alkynyl; $R^2$ is lower alkenyl, lower alkynyl or cycloalkyl; $R^3$ is hydrogen; $R^4$ is alkyl, cycloalkyl or lower alkoxycarbonylalkyl or $R^2$ and $R^3$ are joined to form dimethyleneoxy (i.e. —CH$_2$OCH$_2$—) or $R^3$ and $R^4$ taken together with the nitrogen to which they are attached, form a 5- to 6-membered heterocyclic ring, compositions containing said compounds and a method of employing said compounds as arthropod repellents.

4 Claims, No Drawings

ARTHROPOD REPELLENTS

This is a division of application Ser. No. 056,179 filed July 10, 1979, now U.S. Pat. No. 4,389,401.

The search for insect repellents which have a combination of excellent repellency, high residual activity and essentially no toxicity is a continuing one due to recognition of the possible toxicity to animals or humans of many known insecticides. Since long lasting repellents provide essentially the same results as an insecticide and they also avoid the toxicity problems compounds having these effects are in great demand.

Accordingly, it is an object of this invention to provide novel compounds for repelling arthropods, also novel compositions useful in repelling arthropods and methods for repelling arthropods including stable flies, mosquitoes, cockroaches and the like.

The novel compounds of this invention have the following structural formula:

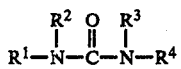

wherein $R^1$ is alkenyl for example, alkenyl containing at least 3 carbon atoms, such as, lower alkenyl of from 3 to 7 carbon atoms, such as, allyl, 2-methylallyl, 1-butenyl, 1-pentenyl, 1-hexenyl 1-heptenyl and the like; alkynyl, for example, of at least 3 carbon atoms, such as, lower alkynyl of from 3 to 7 carbon atoms such as 2-propynyl, 2-butynyl; 2-pentynyl, 2-hexynyl, 2-heptynyl and the like; $R^2$ is alkenyl as defined above, alkynyl as defined above, cycloalkyl, for example, cyclo lower alkyl of from 5 to 7 carbon atoms such as cyclopentyl, cyclohexyl, cycloheptyl and the like, phenyl lower alkyl such as benzyl, phenethyl, phenylpropyl and the like; $R^3$ is hydrogen and $R^4$ is alkyl, for example, lower alkyl of from 1 to 8 carbon atoms as methyl, ethyl, propyl, butyl, pentyl, hexyl, heptyl, octyl and the like; cycloalkyl for example cyclo lower alkyl of from 5 to 7 carbon atoms, alkoxycarbonylalkyl for example lower alkoxycarbonyl lower alkyl such as methoxycarbonylmethyl, ethoxycarbonylmethyl, propoxycarbonylmethyl, butoxycarbonyl-methyl and the like or $R^2$ and $R^3$ are joined to form dimethyleneoxy (i.e. —CH$_2$OCH$_2$—), or $R^3$ and $R^4$, taken together with the nitrogen atom to which they are attached, may be joined to form a 5- to 7-membered heterocyclic ring such as pyrrolidyl, piperdyl and the like.

A preferred embodiment of this invention relates to novel compounds having the formula:

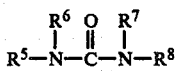

wherein $R^5$ is allyl, 2-methylallyl or 2-propynyl; $R^6$ is allyl, 2-methylallyl or cyclohexyl; $R^7$ is hydrogen; $R^8$ is lower alkyl or lower alkoxycarbonylmethyl or $R^6$ and $R^7$ are joined to form dimethyleneoxy or $R^7$ and $R^8$ taken together with the nitrogen to which they are attached are joined to form pyrrolidyl. Especially preferred are those compounds wherein $R^5$ are $R^6$ are 2-methylallyl. These compounds exhibit particularly good insect repellent action.

Products of this invention excluding those compounds where $R^2$ and $R^3$ are joined to form dimethyleneoxy and those where $R^3$ and $R^4$ are joined to form a heterocycle are prepared by treating an appropriately substituted amine (II, infra) with an appropriately substituted isocyanate (III, infra). The following equation illustrates this process:

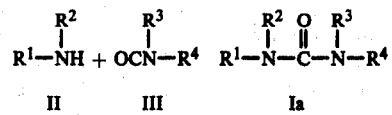

wherein $R^1$, $R^2$, $R^3$ and $R^4$ are as defined above.

The reaction with the amine (II, supra) and the isocyanate (III, supra) may be conducted in any solvent which is inert or substantially inert to the reactants such as ethers including diethylether, tetrahydrofuran and the like. The reaction may be conducted at a temperature in the range of from about 0° to about 100° C. for a period of time from about 15 minutes to about 3 hours; however, the reaction is generally initiated at room temperature and conducted at room temperature for a period of time of about 1 hour.

Those compounds wherein $R^3$ and $R^4$ are joined together with the nitrogen atom to which they are attached to form a heterocyclic ring are prepared by treating an appropriately substituted amine with an appropriately substituted acid chloride. The following equation illustrates this process:

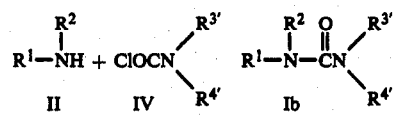

wherein $R^1$ and $R^2$ are as defined above and $R^{3'}$ and $R^{4'}$ are joined together with the nitrogen to which they are attached to form a 5 to 7-membered heterocyclic ring.

The reaction of the amine (II, supra) with the acid chloride (IV, supra) may be conducted in any solvent which is inert or substantially inert to the reactant such as toluene, benzene, hexane, acetonitrile, carbon tetrachloride, and the like. The reaction may be conducted at a temperature in the range of from about 0° to about 100° C. for a period of time of from about 1 to about 5 hours; however, the reaction is generally initiated at room temperature and conducted at room temperature for about 3 hours.

Those compounds wherein $R^2$ and $R^3$ are joined to form a radical of the formula, —CH$_2$OCH$_2$— are prepared by reacting the compounds of formula I wherein $R^2$ and $R^3$ are hydrogen with paraformaldehyde in the presence of an organic acid such as p-toluene sulfonic acid and the like and azeotroping the water formed during the reaction by employing an appropriate solvent such as benzene, chloroform and the like.

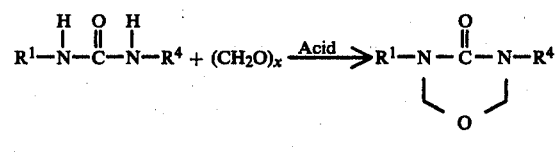

The compounds of this invention (I, supra) and compositions thereof can be employed over a wide range of concentration in a variety of carriers or diluents conventionally used in the art.

The amount of compound employed in the insect repellent compositions can vary between from about 0.1 to about 90 weight percent basis of the weight of the composition and will depend upon the intended use. Usually, the compositions contain between about 0.1 to about 10 weight percent of one or more of the compounds, hereinbefore described, and the compound is usually in intimate mixture with the carrier.

When it is desired to use the insect repellent composition directly (i.e., without further dilution), the amount of the compound used can usually vary from between about 0.1 to 5.0 weight percent. When it is desired to formulate a concentrated composition, i.e., one suitable for dilution prior to end use, the compounds will usually be present in the composition in an amount of from about 0.5 to about 90 weight percent.

The carrier employed can be any carrier conventionally used in insect repellent formulations. The carrier should also be one that will not be harmful to the environment. The carrier can be any one of a variety of organic and inorganic liquid, solid, or semi-solid carriers or carrier formulations conventionally used in insect repellent products and can be a mixture of such carriers.

Examples of organic liquid carriers include liquid aliphatic hydrocarbons such as pentane, hexane, heptane, nonane, decane and their analogs, as well as liquid aromatic hydrocarbons. Examples of other liquid hydrocarbons include oils produced by the distillation of coal and the distillation of various types and grades of petrochemical stocks including kerosene oils which are obtained by fractional distillation of petroleum at between 84° C. and 130° C. and which usually have a flash point between 18° C. and 32° C.

Other petroleum oils include those generally referred to in the art as agricultural spray oils which are light and medium spray oils consisting of the middle fractions in the distillation of petroleum and have a viscosity in the range of from about 40 to 85 sec. Saybolt at 4° C. and are only slightly volatile. These oils are usually highly refined and contain only minute amounts of unsaturated compounds are measured by standard sulfonation tests. The customary sulfonation range of such oils is between 90% and 94% of unsulfonatable residue. These oils are paraffin oils and can be emulsified with water and an emulsifier and diluted to lower concentrations and used as sprays. Tall oils obtained from sulfate digestion of wood pulp, like paraffin oils, also can be employed.

In addition to the above-mentioned liquid hydrocarbons, the carrier can contain conventional emulsifying agents (e.g., a non-ionic surfactant such as an ethylene oxide condensate of octyl phenol or an anionic surfactant such as an alkali metal salt of an alkylbenzenesulfonic acid). Such emulsifiers are used to permit the composition to be dispersed in and diluted with water for end use application.

When paraffin oils are employed as carriers in the insect repellent compositions of this invention, they are usually used in conjunction with an emulsifier, the mixture being diluted with water immediately prior to the end-use application. Other suitable paraffin oils, particularly those used with emulsions, are referred to in the art as heavy paraffin oils and usually have a viscosity greater than 85 sec. Saybolt at 4° C.

Other advantageous organic liquid carriers can include liquid terpene hydrocarbons and terpene alcohols such as alpha-pinene, dipentene, terpineol, and the like. Still other liquid carriers include organic solvents such as aliphatic and aromatic alcohols, esters, aldehydes, and ketones. Aliphatic monohydric alcohols include methyl, ethyl, n-propyl, isopropyl, n-butyl, sec-butyl and t-butyl alcohols. Suitable dihydric alcohols include glycols such as ethylene and propylene glycol and the pinocols (alcohols having the empirical formula: $C_6H_{12}(OH)_2$). Suitable polyhydroxy alcohols include glycerol, arabitol, erythritol, sorbitol, and the like. Suitable cyclic alcohols include cyclopentyl and cyclohexyl alcohols.

Conventional aromatic and aliphatic esters, aldehydes and ketones can be employed and are usually used in combination with the above-mentioned alcohols. Still other liquid carriers including high-boiling petroleum products, such as mineral oil and higher alcohols, such as cetyl alcohol can also be employed. Additionally, conventional "stabilizers" or "synergizers" such as t-butyl sulfinyl dimethyl dithiocarbamate, can be employed in conjunction with, or as a component of, the carriers comprising the compositions of this invention.

Solid carriers which can be used in the compositions of this invention include finely divided organic and inorganic solid materials. Suitable finely divided solid inorganic carriers include siliceous minerals such as clay, including bentonite, attapulgite, fuller's earth, diatomaceous earth, kaolin, mica, talc, finely divided quartz, and the like, as well as synthetically prepared siliceous materials, such as silica aerogels and precipitated and fume silicas.

Examples of finely divided solid organic materials include cellulose, sawdust, synthetic organic polymers and the like.

Examples of semi-solid carriers include petroleum jelly, lanolin and the like, and the mixtures of liquid and solid carriers which provide semi-solid carrier products.

The above-described compositions can be employed per se or can be diluted with suitable liquids or solids to repel common flying and crawling insect pests, such as roaches, moths, house and stable flies, termites, flour beetles, bean beetles, weevils, ticks, chinch bugs, lice, ants, chiggers, mosquitoes and the like. The compositions, when used to contact an insect environment, effectively repel the insects. By way of example, one advantageous embodiment of a composition of this invention comprises from about 0.1 to about 90 percent, preferably 0.1 to about 10 percent by weight of an active compound falling within the scope of this invention, in intimate mixture with one or more of the above-mentioned carriers.

Insect pests can be repelled by contacting the surfaces on which the insects may alight or crawl such as clothing, tents, skin and the like with a liquid, solid or semi-solid compositions. The contact can be accomplished directly (e.g., by atomizing the composition into the air as a liquid or as a dust so that the material will fall on the desired surface).

By way of further example, insect-infested animals, such as dogs with fleas or poultry with lice, cows with ticks may be treated with the insect repellent compositions by contacting the fur and/or or feathers and the lice, fleas and ticks contained therein, thereby ending the insect infestation. Also, granaries and silos can be treated with the compositions of this invention, prior to grain storage, to prevent beetle, weevil, and other insect infestations in the grain to be subsequently stored. Food packaging elements or containers including fiber, cardboard or wooden shipping containers or storage bins, flous sacks, and the like, can be treated with the compositions of this invention to prevent insect infestation.

The following examples illustrate the preparation of the compounds of this invention; however, it is to be understood that wide modifications and variations may be employed to arrive at the compounds of this invention.

EXAMPLE 1

N,N-Diallyl-N'-ethylurea

To a 100 milliliter 3 necked flask fitted with a stirrer, condenser and dropping funnel is added diallylamine (9.7 grams; 0.1 mole) and diethylether (50 milliliters). Ethyl isocyanate (7.1 grams; 0.1 mole) in diethyl ether (10 milliliters) is then added dropwise with cooling. The reaction mixture is stirred at room temperature for one hour and the ether removed to afford 16 grams of N,N-diallyl-N-ethyl urea a yellow oil.

By following substantially the procedure of Example 1 and by employing the appropriate starting materials as illustrated in Table I the following compounds are prepared.

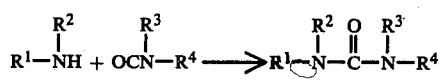

TABLE I

| Ex. No. | $R^1$ | $R^2$ | $R^3$ | $R^4$ |
|---|---|---|---|---|
| 2 | $CH_2=CHCH_2-$ | $CH_2=CHCH_2-$ | H | $-C_3H_7$ |
| 3 | " | " | H | $-C_4H_9$ |
| 4 | " | " | H | $-CH_2CO_2C_2H_5$ |
| 5 | " | " | H | $-CH_2CO_2C_4H_9-n$ |
| 6 | $CH_2=\overset{CH_3}{\underset{|}{C}}CH_2-$ | $CH_2=\overset{CH_3}{\underset{|}{C}}CH_2-$ | H | $-C_3H_7$ |
| 7 | " | " | H | $-C_4H_9$ |
| 8 | " | " | H | $-CH_2CO_2C_2H_5$ |
| 9 | " | " | H | $-CH_2CO_2C_4H_9$ |
| 10 | $CH\equiv CCH_2+$ | $CH_3$ | H | $-C_3H_7$ |
| 11 | $CH\equiv CCH_2$ | $CH_3$ | " | $-C_4H_9$ |
| 12 | $CH\equiv CCH_2$ | $CH_3$ | " | $-CH_2CO_2C_2H_5$ |
| 13 | $CH\equiv CCH_2$ | $CH_3$ | " | $-CH_2CO_2C_4H_9$ |
| 14 | $CH_2=CHCH_2-$ | 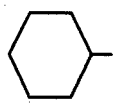 | " | $CH_3$ |
| 15 | " | " | " | $-C_2H_5$ |
| 16 | " | " | " | $-C_3H_7$ |
| 17 | " | " | " | $-CH_2CO_2C_2H_5$ |
| 18 | " | " | " | $-CH_2CO_2C_4H_9$ |

EXAMPLE 19

N Allyl-N-cyclohexyl-N'-tetramethyleneurea

In a 100 milliliter 3-necked round bottom flask equipped with a stirrer, condenser and a dropping funnel is added carbamoyl chloride (9.3 grams; 0.07 moles, triethylamine (7.1 grams; 0.0 moles) and toluene (15 milliliters). To this solution is added dropwise allylcyclohexylamine (10.0 grams; 0.07 moles). Reaction mixture is warmed to 45° C. and then stirred at room temperature for 3 hours. The amine hydrochloride is filtered off and the solvent removed to afford 13 grams of N-(allyl)-N-cyclohexenyl-N'-tetramethylene urea.

EXAMPLE 20

N,N-bis-(2-methallyl)-N'-tetramethyleneurea

In a 100 milliliter 3 necked round bottom flask fitted with a stirrer, condenser and dropping funnel is added carbamoyl chloride (5.3 grams; 0.04 moles) triethylamine (4.0 grams; 0.04 moles and toluene (60 milliliters). To this solution is added dropwise bis-(2-methallylamine) (5.0 grams; 0.04 mole). The reaction mixture is warmed to 45° C. and stirred at room temperature for 3 hours. The amine hydrochloride is collected by filtration and the toluene removed to afford 8 grams of N,N-bis-(2-methallyl)-N'-tetra-methyleneurea.

By following substantially the procedure described in Examples 19 and 20 the following equation taken together with Table II illustrates the starting materials and final products which may be obtained by this process.

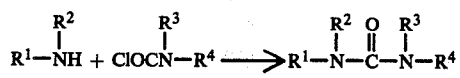

TABLE II

| Ex. No. | $R^1$ | $R^2$ | $R^3$ | $R^4$ |
|---|---|---|---|---|
| 21 | $CH_2=\overset{CH_3}{\underset{|}{C}}CH_2$ | $CH_3$ | | $-CH_2CH_2CH_2CH_2-$ |
| 22 | " | $\phi CH_2$ | | " |

EXAMPLE 23

Tetrahydro-3-hexyl-5-allyl-4H 1,3,5-oxadiazin-4-one

In a 300 ml, 3-necked flask equipped with a stirrer, condenser and dropping funnel is added N-hexyl-N-allyl urea (18.4 g; 0.1 mole), paraformaldehyde (6.0 g; 0.2 mole), p-toluenesulfonic acid (1.0 g) and chloroform (150 ml). The reaction mixture is heated to reflux and 1.8 ml of water is collected. The reaction mixture is cooled to room temperature, neutralized with sodium hydroxide and washed with water. The chloroform solution is dried over magnesium sulfate, and filtered. The chloroform is removed and the residue distilled to afford 15 grams of tetrahydro-3-hexyl-5-allyl-4H 1,3,5-oxadiazin-4-one h.p. 105°–112° C./0.6 mm.

By following substantially the procedure of Example 23 the following equation taken together with Table III illustrates the starting materials and final products which may be obtained following said procedure.

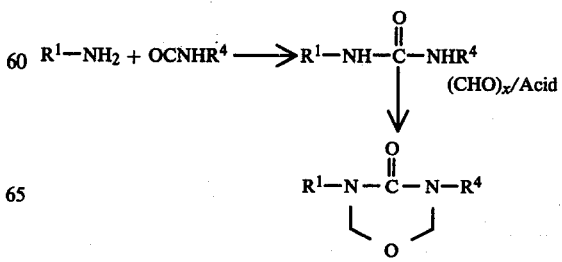

TABLE III

| Ex. No. | R¹ | R² | Boiling Point °C./mm |
|---|---|---|---|
| 24 | CH$_2$=CHCH$_2$— | —C$_2$H$_5$ | 95/0.5 |
| 25 | " | —C$_3$H$_7$—n | 80/1 |
| 26 | " | —C$_4$H$_9$—n | 90/.75 |
| 27 | " | —(CH$_2$)$_4$CH$_3$ | — |
| 28 | " |  | 113/.5 |
| 29 | CH$_2$=C(CH$_3$)—CH$_2$ | —C$_2$H$_5$ | 75/1.5 |
| 30 | " | —C$_3$H$_7$—n | 73/1.7 |
| 31 | " | —C$_4$H$_9$—n | 61/1.7 |
| 32 | " | —(CH$_2$)$_7$CH$_3$ | 93/.5 |
| 33 | " |  | 75/1.5 |

The following test description and results illustrate the use of the novel compounds of this invention.

REPELLENCY SCREEN

Male albino guinea pigs (Perfection Breeders) are divided into groups of 2 each and placed into individual cages in a rodent battery equipped with an automatic watering system. Individual animal body weights ranged from 450 to 600 g. Feed and water were provided ad libitum. Guinea pigs are prepared for testing by clipping a patch of hair from the back with a size 10 clipper blade. This permits a residual amount of hair to be left on the animal.

Test compounds are formulated as 5% solutions in acetone. A 2.5 ml. volume of test solution is applied with a medicine dropper pipette to an area on the animal's back measuring approximately 7 cm. ×5 cm. This application results in a deposit rate of 3.5 mg./cm.$^2$. Two guinea pigs are treated with each compound. The test animal is anesthetized with sodium pentobarbital administered intraperitoneally at the rate of 35 mg./kg. and is placed in a cylindrical plastic cage with only the treated portion of the back exposed. The masked animal is introduced into an insect cage filled with either starved stable flies or yellow fever mosquitoes. Approximately 500-1000 insects were used as the challenge. The treated guinea pigs is exposed to the test insects for a 5-10 minute period initially and at 3 hours post-treatment and then on a daily basis until the repellency activity of the compound terminates. The residual repellency activity of a compound is regarded as terminated when three or more test insects fed on the guinea pig during the exposure period. N.A. means not active at the test dose.

| | Protection Time | |
|---|---|---|
| Example No. | Stable Fly | Yellow Fever Mosquito |
| 1 | 3 Hours (H) | 3 Hours (H) |
| 2 | 1 Day (D) | 1 Day (D) |
| 3 | 2D | 3D |
| 4 | 0.5H | NA |
| 5 | 1D | 1D |
| 6 | 2D | 2D |
| 7 | 4+D | 4+D |
| 8 | 0.5H | 0.5H |
| 9 | 0.5H | 0.5H |
| 10 | 0.5H | 0.5H |
| 11 | 3H | 1D |
| 12 | 3H | 3H |
| 13 | 0.5H | 0.5H |
| 14 | 4+D | 4+D |
| 15 | 4+D | 4+D |
| 16 | 4+D | 4+D |
| 17 | 4+D | 4+D |
| 18 | 0.5H | 0.5H |
| 23 | 4D | 5D |
| 24 | 3H | 3H |
| 25 | 3H | 3H |
| 26 | 2D | 2D |
| 27 | 3D | 4+D |
| 28 | 1D | 1D |
| 29 | 1D | 1D |
| 30 | 1D | 1D |
| 31 | 2D | 3D |
| 32 | 3D | 4+D |
| 33 | 1D | 1D |

What is claimed is:

1. A method for repelling arthropods which comprises applying to an appropriate surface an effective amount of N,N-bis-2-methyl-allyl-N'-propylurea.

2. A method for repelling arthropods which comprises applying to an appropriate surface an effective amount of N,N-bis-2-methyl-allyl-N'-butylurea.

3. A method for repelling arthropods which comprises applying to an appropriate surface an effective amount of tetrahydro-3-octyl-5-(2'-methylallyl)-4H-1,3,5-oxadiazin-4-one.

4. A method for repelling arthropods which comprises applying to an appropriate surfact an effective amount of tetrahydro-3-hexyl-5-allyl-4H-1,3,5-oxadiazin-4-one.

* * * * *